United States Patent
Burton (10) Patent No.: US 8,585,959 B2
(45) Date of Patent: *Nov. 19, 2013

(54) BALLOON WITH INTEGRALLY RETAINED DILATION ELEMENT

(75) Inventor: David G. Burton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 281 days.

This patent is subject to a terminal disclaimer.

(21) Appl. No.: 12/895,358

(22) Filed: Sep. 30, 2010

(65) Prior Publication Data

US 2012/0083821 A1 Apr. 5, 2012

(51) Int. Cl.
  *B29C 39/02* (2006.01)
(52) U.S. Cl.
  USPC ........... 264/532; 264/535; 264/541; 606/190; 606/191; 606/192; 606/194
(58) Field of Classification Search
  CPC .......... A61M 25/1029; A61M 25/104; A61M 25/1002; A61M 29/02
  USPC ................ 264/523, 320, 532–535, 540–541; 425/524, 529, 530, 531, 535; 604/19, 604/96.01, 98.01, 103, 103.01, 103.02, 604/103.03; 606/194, 190–192
  See application file for complete search history.

(56) References Cited

U.S. PATENT DOCUMENTS

| | | | |
|---|---|---|---|
| 4,409,177 A * | 10/1983 | Berth et al. | 264/531 |
| 4,796,629 A | 1/1989 | Grayzel | |
| 5,196,024 A * | 3/1993 | Barath | 606/159 |
| 5,336,178 A | 8/1994 | Kaplan et al. | |
| 5,342,301 A | 8/1994 | Saab | |
| 5,411,478 A | 5/1995 | Stillabower | |
| 5,456,666 A | 10/1995 | Campbell et al. | |
| 5,458,572 A | 10/1995 | Campbell et al. | |
| 5,746,968 A * | 5/1998 | Radisch, Jr. | 264/529 |
| 6,592,550 B1 * | 7/2003 | Boatman et al. | 604/103.06 |
| 6,676,692 B2 | 1/2004 | Rabkin et al. | |
| 6,875,197 B1 | 4/2005 | Simhambhatla et al. | |
| 7,008,438 B2 * | 3/2006 | O'Brien | 606/159 |
| 7,258,696 B2 * | 8/2007 | Rabkin et al. | 623/1.11 |
| 7,354,419 B2 | 4/2008 | Davies, Jr. et al. | |
| 8,043,313 B2 * | 10/2011 | Krolik et al. | 606/159 |
| 8,211,354 B2 * | 7/2012 | Burton | 264/532 |

(Continued)

FOREIGN PATENT DOCUMENTS

| | | |
|---|---|---|
| DE | 10010467 A1 | 9/2001 |
| EP | 1 008 363 A2 | 11/1999 |
| WO | WO 01/60443 A1 | 8/2001 |

OTHER PUBLICATIONS

U.S. Appl. No. 61/332,384, filed May 7, 2010, Hennessey.

(Continued)

*Primary Examiner* — Katherine Dowe
*Assistant Examiner* — Kendra Obu
(74) *Attorney, Agent, or Firm* — Brinks Gilson Lione (57) ABSTRACT

A balloon catheter is provided with integral tubular extensions for securing dilation elements to the outside of the balloon. The dilation elements are disposed within the tubular extensions along the working diameter of the balloon. The balloon may be manufactured by extruding a parison and blow molding the parison with the dilation elements installed within the tubular extensions.

20 Claims, 3 Drawing Sheets

(56) References Cited

U.S. PATENT DOCUMENTS

| | | |
|---|---|---|
| 2005/0119678 A1* | 6/2005 | O'Brien et al. ............... 606/159 |
| 2007/0129751 A1 | 6/2007 | Muni et al. |
| 2007/0205539 A1* | 9/2007 | Chen et al. .................... 264/529 |
| 2008/0086084 A1* | 4/2008 | Schaeffer et al. ........ 604/103.12 |
| 2008/0103444 A1* | 5/2008 | Jimenez .................. 604/103.09 |
| 2008/0228139 A1 | 9/2008 | Melsheimer et al. |
| 2009/0171283 A1* | 7/2009 | Schaeffer et al. ........ 604/103.08 |
| 2009/0171284 A1* | 7/2009 | Burke et al. ................. 604/104 |
| 2009/0234283 A1 | 9/2009 | Burton et al. |
| 2009/0318863 A1 | 12/2009 | Chen |
| 2010/0022950 A1 | 1/2010 | Anderson et al. |

OTHER PUBLICATIONS

U.S. Appl. No. 12/782,432, filed May 18, 2010, Burton.
Search Report and Written Opinion for related PCT/US2011/052080 filed Sep. 19, 2011, mailed Nov. 21, 2011.

* cited by examiner

BALLOON WITH INTEGRALLY RETAINED DILATION ELEMENT

BACKGROUND

The present invention relates generally to medical devices and particularly to a balloon catheter with integral extensions on the surface of the balloon for securing a dilation element.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, vascular angioplasty using a balloon catheter has drawn particular attention from the medical community because of the growing number of people suffering from vascular problems associated with arterial stenosis. This has lead to an increased demand for medical procedures to treat such problems. The widespread frequency of vascular problems may be due to a number of societal changes, including the tendency of people to exercise less while eating greater quantities of unhealthy foods, in conjunction with the fact that people generally now have longer life spans than previous generations. Angioplasty procedures have become a popular alternative for treating arterial stenosis because angioplasty procedures are considerably less invasive than other alternatives. As an example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for vascular treatments, the medical community has turned to angioplasty procedures, in combination with stenting and other procedures, to avoid the problems associated with traditional open surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the artery to be treated. During this stage, the balloon is uninflated and collapsed onto the shaft of the catheter in order to present a low profile which may be passed through the vasculature. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. Alternatively, if the balloon catheter is not adapted for delivery of a stent, either a balloon-expandable stent or a self-expandable stent may be implanted in the dilated region in a follow-up procedure. Although the treatment of stenosed arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. One solution that has been offered for dilating hardened stenoses is special balloon catheters with dilation wires or beads that extend along the length of the balloon. The dilation wires and/or beads focus that dilation pressure of the balloon onto the narrower contact area between the dilation wire or bead and the vessel wall. As a result, the increased, focused pressure may crack and/or break up the hardened stenosis, thereby allowing the vessel lumen to be expanded.

One approach that has been used to attach dilation wires and/or beads to a balloon is securing the wires and/or beads to the exterior surface of the balloon with adhesives. However, the use of adhesives to secure dilation wires and/or beads has several disadvantages. For example, there may be concern that the adhesive could detach from the balloon surface and allow the dilation wire and/or bead to break loose. This may be a particular concern when the adhesive is the only or the primary mechanism for securing the dilation wire and/or bead to the balloon surface. Detachment of the adhesive from the balloon surface can be a more serious problem when the balloon is made of a compliant or semi-compliant material, because the balloon material stretches as the balloon expands but the dilation wire and/or bead may not stretch during expansion or may stretch at a different rate. Because of these opposing forces between the balloon material and the dilation wire and/or bead, the adhesive may crack or lose its adherence to the balloon surface. Moreover, even in the case of non-compliant balloons, detachment of the adhesive may be a concern because physicians are particularly adverse to any possible risk of intravascular device failures. Thus, a mechanism for more securely attaching dilation wires and/or beads to a balloon surface would be desirable.

In addition, the use of adhesives in a manufacturing setting is disadvantageous. Applying adhesives during the manufacturing process is typically a manually intensive task and time consuming. Maintaining cleanliness standards is also more difficult with the presence of adhesives, since adhesives are generally messy. The use of adhesives also requires extra fixturing to temporarily secure the parts being adhered while the adhesive cures.

Accordingly, the inventor believes it would be desirable to provide a balloon catheter with a mechanism that is integral with the balloon for securing a dilation wire and/or bead to the balloon surface.

SUMMARY

A balloon catheter is described that has an integral tubular extension along the length of the balloon for securing a dilation element to the balloon. The balloon may be made from an extruded parison with the tubular extensions integrally extruded with the parison. The dilation elements may be installed into the tubular extensions after the parison is extruded. The balloon may be formed by blow molding the parison.

The invention may include any of the following aspects in various combinations and may also include any other aspect described below in the written description or in the attached drawings.

A method of forming a balloon for a balloon catheter, comprising:
extruding a parison having a uniform shape along an entire length thereof, the parison comprising a central opening and a longitudinal tubular extension extending from an exterior surface of the parison, the tubular extension defining a longitudinal cavity bounded circumferentially and longitudinally by a wall of the tubular extension;
disposing a dilation element into the longitudinal cavity of the tubular extension through an end opening thereof; and
heating the parison inside a mold and pressurizing the central opening, the parison thereby expanding against the mold, wherein an outer portion of the wall is compressed against the mold, and the dilation element extends along a length of a working diameter of the balloon.

The method wherein the mold comprises a clearance cavity receiving the tubular extension along a working diameter portion.

The method wherein the mold comprises a clearance cavity at least partially receiving the tubular extension along a neck region, the clearance cavity in the neck region thereby indexing the parison to the clearance cavity along the working diameter portion.

The method further comprising disposing heat shrink tubing over the tubular extension along the neck region after the heating and pressurizing, the tubular extension along the neck region thereby being substantially reformed into the exterior surface of the parison.

The method further comprising stretching the parison while the parison is heated after the dilation element is disposed into the tubular extension and before the parison is pressurized, the tubular extension thereby shrinking diametrically against the dilation element.

The method wherein the mold does not comprise any clearance cavities receiving the tubular extension along a tapered region extending to a neck region, the tubular extension thereby being compressed against the mold and substantially closing the longitudinal cavity along the tapered region.

The method wherein a first outer width across the tubular extension between the longitudinal cavity and the exterior surface of the parison is less than a second outer width across the tubular extension across the longitudinal cavity, the first outer width isolating the tubular extension during the heating and pressurizing to minimize reshaping of the tubular extension during the heating and pressurizing.

The method wherein the dilation element is entirely sealed within the tubular extension, the tubular extension being characterized by not comprising any lateral openings through the wall of the tubular extension.

The method wherein the dilation element comprises a round cross-section.

The method wherein the dilation element comprises a non-round cross-section.

The method wherein the dilation element is entirely sealed within the tubular extension, the tubular extension being characterized by not comprising any lateral openings through the wall of the tubular extension, the mold comprising a clearance cavity receiving the tubular extension along a working diameter portion, and further comprising stretching the parison while the parison is heated after the dilation element is disposed into the tubular extension and before the parison is pressurized, the tubular extension thereby shrinking diametrically against the dilation element.

The method wherein the mold does not comprise any clearance cavities receiving the tubular extension along a tapered region extending to a neck region, the tubular extension thereby being compressed against the mold and substantially closing the longitudinal cavity along the tapered region, and the mold comprising a clearance cavity at least partially receiving the tubular extension along the neck region, the clearance cavity in the neck region thereby indexing the parison to the clearance cavity along the working diameter portion.

The method further comprising disposing heat shrink tubing over the tubular extension along the neck region after the heating and pressurizing, the tubular extension along the neck region thereby being substantially reformed into the exterior surface of the parison, wherein a first outer width across the tubular extension between the longitudinal cavity and the exterior surface of the parison is less than a second outer width across the tubular extension across the longitudinal cavity, the first outer width isolating the tubular extension during the heating and pressurizing to minimize reshaping of the tubular extension during the heating and pressurizing, and the dilation element comprising a round cross-section.

A balloon catheter, comprising:
a balloon mounted on a catheter, the balloon configured to expand from a deflated state to an expanded state;
an integral longitudinal tubular extension disposed along a working diameter length of an exterior surface of the balloon, wherein the tubular extension comprises a longitudinal cavity bounded by a wall of the tubular extension; and
a dilation element disposed within the longitudinal cavity, wherein opposing ends of the dilation element are longitudinally restrained by compressed portions of the tubular extension adjacent the opposing ends.

The balloon catheter wherein a first outer width across the tubular extension between the longitudinal cavity and the exterior surface of the balloon is less than a second outer width across the tubular extension across the longitudinal cavity.

The balloon catheter wherein the dilation element is diametrically squeezed by the wall of the longitudinal extension.

The balloon catheter wherein the dilation element extends substantially the entire length of the working diameter length of the balloon.

The balloon catheter wherein the dilation element is entirely sealed within the tubular extension, the tubular extension being characterized by not comprising any lateral openings through the wall of the tubular extension.

The balloon catheter wherein the dilation element is diametrically squeezed by the wall of the longitudinal extension, and the dilation element extends substantially the entire length of the working diameter length of the balloon.

The balloon catheter wherein the dilation element is entirely sealed within the tubular extension, the tubular extension being characterized by not comprising any lateral openings through the wall of the tubular extension.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
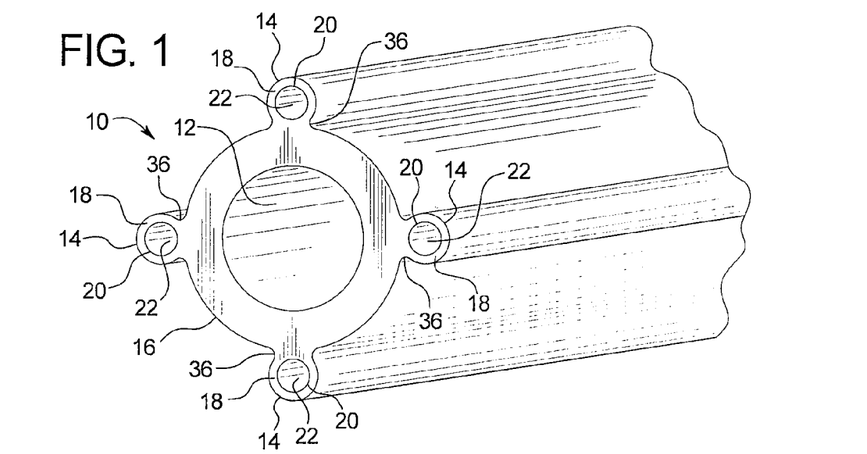
FIG. 1 is a perspective view of an extruded parison.

Referring now to the figures, and particularly to FIG. 1, an extruded parison 10 is shown. The extruded parison 10 may be continuously extruded through a mold from a polymer material, such as nylon. Thus, each of the structures of the extruded parison 10 are integral with each other and extend along the entire length of the extruded parison 10. The extruded parison 10 may have a central opening 12 that is used for blow molding the parison 10 as described below. The central opening 12 will form the inner lumens of the neck regions 68, which are attached to a catheter 66, and will also form the interior of the balloon 64, which allows the balloon 64 to expand from a deflated state to an expanded state.

The extruded parison 10 also includes a tubular extension 14 on the exterior surface 16 that extends longitudinally along the length of the extruded parison 10. The tubular extension 14 has a wall 18 that defines the circumferential boundary of a longitudinal cavity 22 in the tubular extension 14. An opening 20 that communicates with the longitudinal cavity 22 may be provided at each end of the tubular extension 14. The cross-sectional shape of the longitudinal cavity 22 preferably matches the cross-sectional shape of the dilation element 28 described below. In order to allow the dilation element 28 to be inserted into the longitudinal cavity 22, the size of the longitudinal cavity 22 is initially slightly larger than the dilation element 28. The exterior shape of the tubular extension 14 also preferably matches the cross-sectional shape of the dilation element 28. Thus, the thickness of the circumferential wall of the tubular extension 14 may be generally uniform. Preferably, there are no lateral openings through the wall 18 of the tubular extension 14 so that the longitudinal cavity 22 is completely sealed by the wall 18 from the outside except for the openings 20 at the ends of the tubular extension 14. The outer width across the tubular extension 14 may also be narrower between the bottom of the longitudinal cavity 22 and the exterior surface 16 of the parison 10 than it is across the longitudinal cavity 22. In other words, the tubular extension 14 may have a narrowed neck 36 below the longitudinal cavity 22. As described further below, the narrowed neck 36 may be useful to isolate the tubular extension 14 during the blow molding process.

Figure 2:
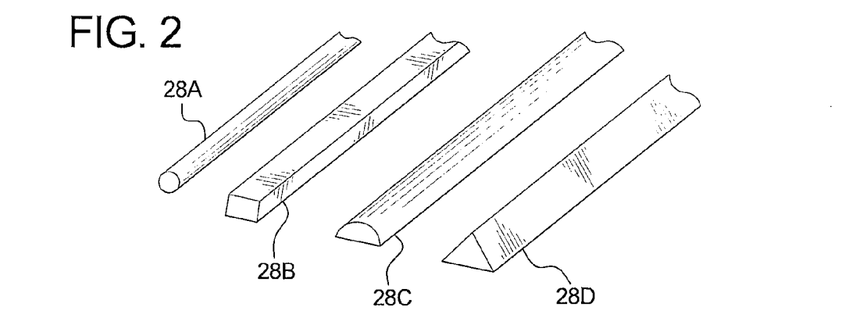
FIG. 2 is a perspective view of different dilation elements.

As shown in FIG. 2, a dilation element 28 may also be provided. The dilation element 28 is preferably made from a different material than the extruded parison 10. For example, the dilation element 28 may be made of a metal to provide hardness and strength to the dilation element 28. The dilation element 28 may be a solid wire, a coiled wire, a continuous wire with regions of reduced cross-sectional area, or may be multiple longitudinally spaced apart wires within a single tubular extension 14. The cross-sectional shape of the dilation element 28 may be modified as desired. For example, the cross-sectional shape of the dilation element 28 may be round like dilation element 28A in FIG. 2 or non-round like dilation elements 28B-D in FIG. 2. As shown, dilation element 28B has a rectangular cross-sectional shape. Dilation element 28C has a half-round cross-sectional shape. Dilation element 28D has a triangular cross-sectional shape. Preferably, the length of the dilation element 28 is significantly longer than the width of the dilation element 28 with a ratio of at least 10:1 or 50:1. Accordingly, the shape of the dilation element 28 may be designed for the particular application and may have a blade shape, bead shape or any other suitable shape for focusing pressure along a discrete longitudinal region.

Figure 3:
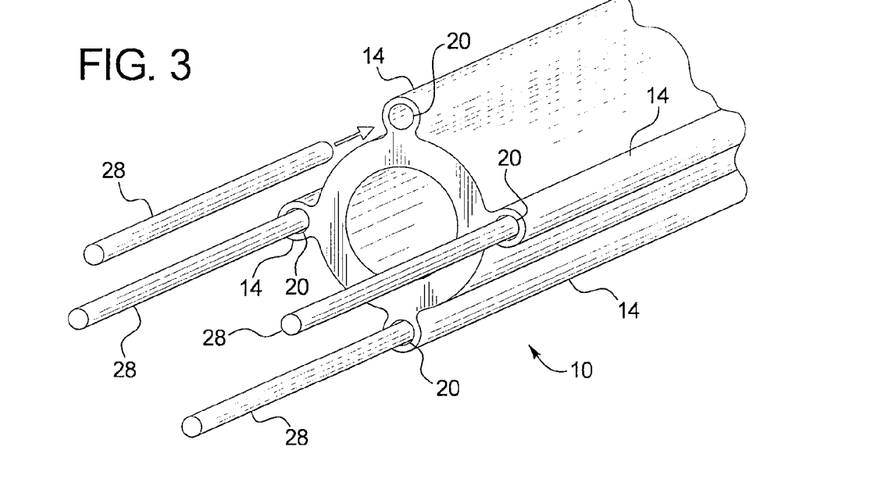
FIG. 3 is a perspective view of dilation elements being disposed within the tubular extensions.

As shown in FIG. 3, after the parison 10 has been extruded, the dilation element 28 is disposed within the tubular extension 14 of the extruded parison 10. Specifically, one end of the dilation element 28 may be inserted through an end opening 20 of the longitudinal cavity 22 and slid through the tubular extension 14. If additional securement of the dilation element 28 is desired, adhesive may be applied within the longitudinal cavities 22 to bond the dilation element 28 to the tubular extension 14. However, it is preferred that no adhesive is used to bond the dilation element 28, since this would add extra cost and difficulty in manufacturing the balloon catheter 72. Although it is preferable for the dilation elements 28 to extend substantially the entire length of the working diameter region 74 of the balloon 64, it is also possible to use shorter dilation elements 28 that extend along only part of the length of the working diameter 74 of the balloon 64. In addition, while a single length of the dilation element 28 may be used along the length of the balloon 64, multiple dilation element sections 28 may also be used to provide flexibility to the finished balloon catheter 72. Although the multiple dilation element sections 28 may be separate from each other, multiple dilation element sections 28 may also be connected together with thin portions to provide flexibility while still providing an element that extends substantially the entire length of the working diameter region 74.

Figure 4:
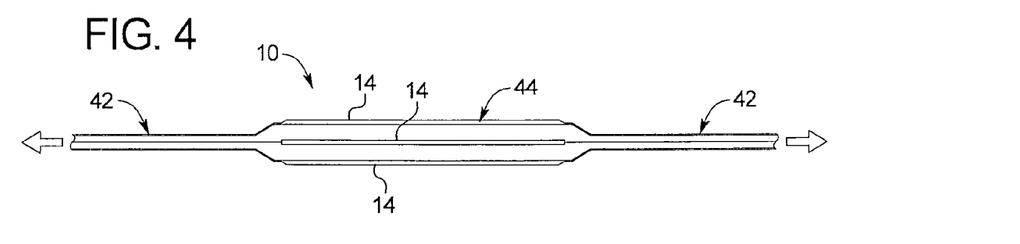
FIG. 4 is a side view of the parison being stretched.

As shown in FIG. 4, it may be preferable to initially stretch a portion 42 of the parison 10 after installing the dilation elements 28 into the tubular extensions 14 of the parison 10. The initial stretching process may be achieved by heating one end 42 of the parison 10 without heating the middle 44 of the parison 10. The heated end 42 of the parison 10 may be pulled to stretch it without causing the middle portion 44 to be stretched. The other end 42 may then be heated and stretched in a similar manner. The initial stretching step may be helpful to define the region of the balloon 64 that will form the expanded balloon 64 after blow molding. The initial stretching step also may help determine the proper longitudinal positioning of the dilation elements 28 within the tubular extensions 14. Alternatively, if the parison 10 is stretched prior to inserting the dilation elements 28, it is preferable that the initial stretching does not significantly change the size of the longitudinal cavities 22 or the end openings 20 so that the dilation elements 28 can be inserted without excessive difficulty.

Figure 5:
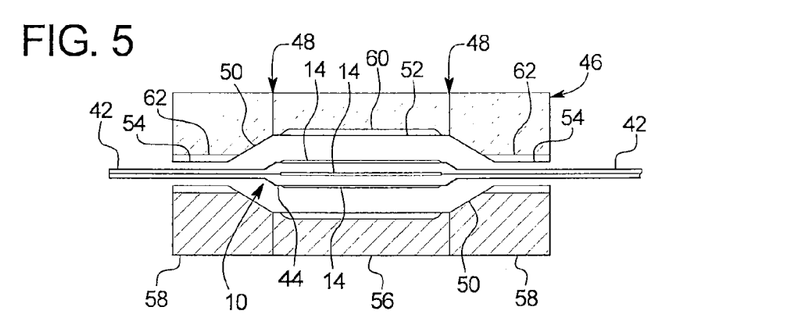
FIG. 5 is a side view of the parison in a mold.

As shown in FIG. 5, the parison 10 may then be positioned within a mold 46 for blow molding. While the mold 46 may take various forms, a three-piece mold 46 may be desirable. The three-piece mold 46 may be split in two places 48 at the transition between the tapered regions 50 and the working diameter 52. The parison 10 may be inserted into the mold 46 by separating one or more of the pieces of the mold 46 and inserting one end 42 of the parison 10 through one of the neck regions 54 in the mold 46. The working diameter piece 56 and/or the other neck piece 58 may then be slid over the other end 42 of the parison 10.

Figure 6:
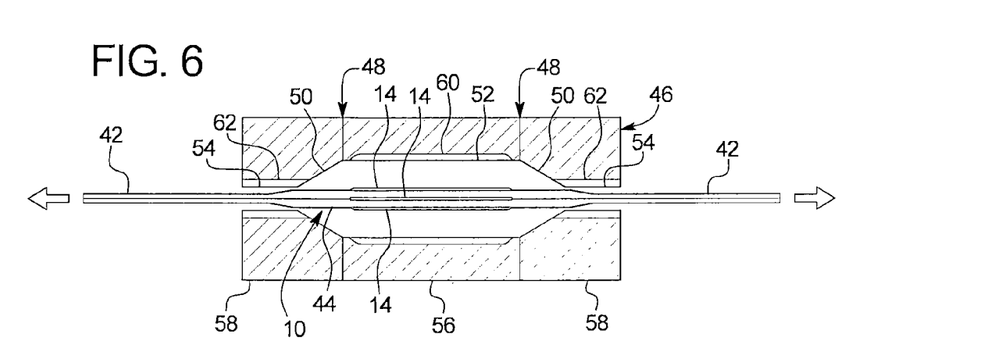
FIG. 6 is a side view of the parison in the mold and being stretched.

As shown in FIG. 6, the parison 10 is preferably heated and stretched with the dilation elements 28 installed without pressurizing the center opening 12 prior to the blow molding. This is done by heating at least the middle portion 44 of the parison 10 and pulling on the ends 42 of the parison 10. Although a larger portion of the parison 10 may be heated, it may be desirable to only heat the portion of the parison 10 where the dilation elements 28 are installed and a small length beyond the ends of the dilation elements 28. The stretching of the middle portion 44 of the parison 10 causes the longitudinal cavities 22 to shrink in size and squeeze against the dilation elements 28. This locks the dilation elements 28 into the tubular extensions 14. The portions of the tubular extension 14 that extend past the ends of the dilation elements 28 may also be partially closed, i.e., compressed, by the stretching step. This can also result in longitudinally securing the dilation elements 28 within the tubular extensions 14.

Figure 7:
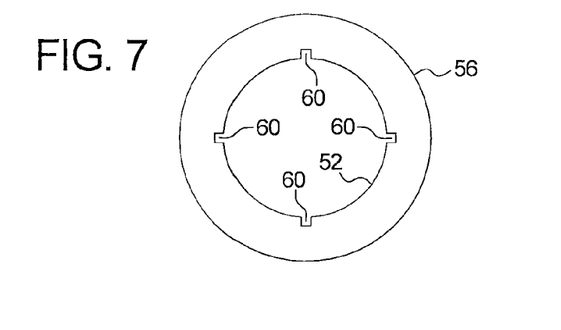
FIG. 7 is an end view of a working diameter piece of the mold.

As shown in FIG. 7, the mold 46 may also have longitudinal clearance cavities 60 along the working diameter 52 that receive the tubular extensions 14 and dilation elements 28. If desired, the working diameter clearance cavity 60 may be sized so that the tubular extension 14 does not significantly contact the mold 46 during blow molding to avoid changing the shape of the tubular extension 14. Alternatively, the working diameter clearance cavity 60 can be sized to contact the tubular extension 14 during blow molding to cause the tubular extension 14 to be reformed into the final desired shape during blow molding. Preferably, the tapered regions 50 of the mold 46 do not have any clearance cavities to receive the tubular extension 14. As a result, when the parison 10 is blow molded, the tubular extensions 14 are compressed against the tapered regions 50 of the mold 46 and are closed and either mostly or entirely reformed into the wall of the finished balloon 64. Similarly, the clearance cavities 60 along the working diameter 52 may be omitted near the ends of the working diameter 52 to compress the tubular extensions 14 adjacent the ends of the dilation elements 28. The neck regions 54 of the mold 46 may or may not have clearance cavities for the tubular extension 14. However, it may be desirable to provide clearance cavities 62 that partially receive the tubular extensions 14 in order to index and align the parison 10 to the mold 46. The neck region clearance cavities 62 may be sized so that they partially reshape the tubular extensions 14 during blow molding to partially reform the tubular extensions 14 into the neck regions 68 of the balloon 64. Once the parison 10 has been indexed to the mold 46 so that the tubular extensions 14 are aligned with the clearance cavities 60, 62, the parison 10 is blow molded in the mold by heating the parison 10 and pressurizing the center opening 12. This causes the parison 10 to circumferentially stretch and expand outward against the walls of the mold 46. If it is desirable to minimize reforming and stretching of the tubular extensions 14 during blow molding, narrowed necks 36 as described above may be used to isolate the tubular extensions 14 from the main body of the parison 10 during blow molding.

Figure 8:
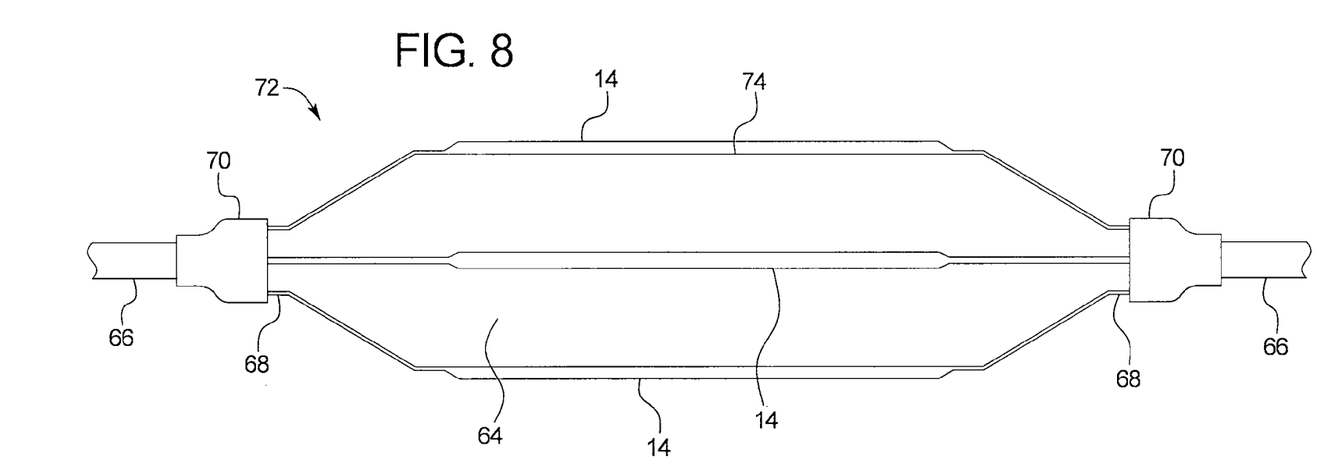
FIG. 8 is a side view of a balloon catheter with the dilation elements.

As shown in FIG. 8, after the parison 10 has been blow molded, the balloon 64 is cooled and removed from the mold 46. The balloon 64 is then mounted onto a catheter 66 by inserting the catheter 66 through the inner lumens of the neck regions 68 of the balloon 64. Preferably, the catheter 66 is bonded and sealed to the neck regions 68 of the catheter 66 by melt bonding. This may be accomplished by disposing heat shrink tubing 70 over the neck regions 68 of the balloon 64. The heat shrink tubing 70, neck regions 68 and catheter 66 are then heated. The heat softens the neck regions 68 and the catheter 66 and causes the heat shrink tubing 70 to shrink and squeeze the neck regions 68 and catheter 66 together. As a result, the neck regions 68 and catheter 66 melt together and adhere to each other when the heat shrink tubing 70, neck regions 68 and catheter 66 cool. In addition, the tubular extensions 14 are substantially reformed into the exterior surface of the neck regions 68 of the balloon 64 by the pressure of the heat shrink tubing 70 and the softening caused by the heat. This provides a smooth attachment between the catheter 66 and the balloon 64 without any significant remnant of the tubular extensions 14 in the neck regions 68.

Figure 9:
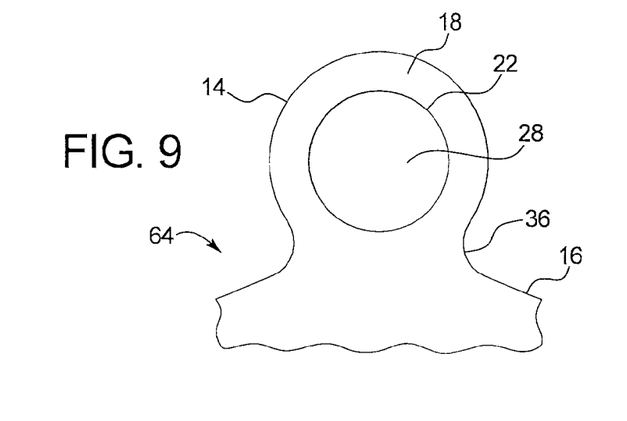
FIG. 9 is a cross-sectional view of the dilation element disposed within the tubular extension.

As shown in FIG. 9, the dilation element 28 is squeezed within the longitudinal cavity 22 of the tubular extension 14 after the balloon 64 has been blow molded. Thus, the blow molding process shrinks the tubular extension 14 around the dilation elements 28 to provide a tight fit between the dilation element 28 and the tubular extension 14. Preferably, the size of the tubular extension 14 is designed to provide an interference fit with the dilation element 28 after the balloon 64 has been blow molded. For example, with a round dilation element 28 having a diameter of 0.010", the initial thickness of the wall 18 of the tubular extension 14 may be about 0.0045", and the thickness of the wall 18 after blow molding the balloon 64 may be about 0.0025". Preferable ranges for the dilation element 28 and the tubular extension 14 are between about 0.005" and about 0.015" for the diameter of the dilation element 28, between about 0.002" and about 0.010" for the initial thickness of the wall 18, and between about 0.001" and about 0.006" for the thickness of the wall 18 after blow molding the balloon 64. The initial clearance between the dilation element 28 and the longitudinal cavity 22 is preferably as small as possible to allow the dilation element 28 to be smoothly inserted into the longitudinal cavity 22. As described above, the narrowed neck 36 of the tubular extension 14 may help to minimize reforming of the tubular extension 14 during blow molding. Although the dilation element 28 need not extend the entire length of the balloon 64 or the working diameter 74 of the balloon 64, it is preferable for the dilation element 28 to extend substantially the entire length of the working diameter 74 of the balloon 64 with the tubular extension 14 being at least partially compressed adjacent opposing ends of the dilation element 28 to longitudinally restrain the dilation element 28. Although a portion of the dilation element 28 may extend past the working diameter 74 of the balloon 64, it may be preferable for the dilation element 28 to extend only along the working diameter 74. It is also preferable for the tubular extension 14 to not have any lateral openings through the wall 18 of the tubular extension 14 so that the dilation element 28 is completely sealed within the longitudinal cavity 22 after blow molding and is not exposed to the outside of the tubular extension 14.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A method of forming a balloon for a balloon catheter, comprising:

extruding a parison having a uniform shape along an entire length thereof, said parison comprising a central opening and a longitudinal tubular extension extending from an exterior surface of said parison, said tubular extension defining a longitudinal cavity bounded circumferentially and longitudinally by a wall of said tubular extension;

disposing a dilation element into said longitudinal cavity of said tubular extension through an end opening thereof;

stretching said parison while said parison is heated after said dilation element is disposed into said tubular extension and before said parison is pressurized, said tubular extension thereby shrinking diametrically against said dilation element; and heating said parison inside a mold and pressurizing said central opening, said parison thereby expanding against said mold, wherein an outer portion of said wall is compressed against said mold, and said dilation element extends along a length of a working diameter of said balloon.

2. The method according to claim 1, wherein said mold comprises a clearance cavity receiving said tubular extension along a working diameter portion.

3. The method according to claim 2, wherein said mold comprises a clearance cavity at least partially receiving said tubular extension along a neck region, said clearance cavity in said neck region thereby indexing said parison to said clearance cavity along said working diameter portion.

4. The method according to claim 3, further comprising disposing heat shrink tubing over said tubular extension along said neck region after said heating and pressurizing, said tubular extension along said neck region thereby being substantially reformed into said exterior surface of said parison.

5. The method according to claim 1, wherein said mold does not comprise any clearance cavities receiving said tubular extension along a tapered region extending to a neck region, said tubular extension thereby being compressed against said mold and substantially closing said longitudinal cavity along said tapered region.

6. The method according to claim 1, wherein a first outer width across said tubular extension between said longitudinal cavity and said exterior surface of said parison is less than a second outer width across said tubular extension across said longitudinal cavity, said first outer width isolating said tubular extension during said heating and pressurizing to minimize reshaping of said tubular extension during said heating and pressurizing.

7. The method according to claim 1, wherein said dilation element is entirely sealed within said tubular extension, said tubular extension being characterized by not comprising any lateral openings through said wall of said tubular extension.

8. The method according to claim 1, wherein said dilation element comprises a round cross-section.

9. The method according to claim 1, wherein said dilation element comprises a non-round cross-section.

10. The method according to claim 1, wherein said dilation element is entirely sealed within said tubular extension, said tubular extension being characterized by not comprising any lateral openings through said wall of said tubular extension, said mold comprising a clearance cavity receiving said tubular extension along a working diameter portion, and further comprising stretching said parison while said parison is heated after said dilation element is disposed into said tubular extension and before said parison is pressurized, said tubular extension thereby shrinking diametrically against said dilation element.

11. The method according to claim 10, wherein said mold does not comprise any clearance cavities receiving said tubular extension along a tapered region extending to a neck region, said tubular extension thereby being compressed against said mold and substantially closing said longitudinal cavity along said tapered region, and said mold comprising a clearance cavity at least partially receiving said tubular extension along said neck region, said clearance cavity in said neck region thereby indexing said parison to said clearance cavity along said working diameter portion.

12. The method according to claim 11, further comprising disposing heat shrink tubing over said tubular extension along said neck region after said heating and pressurizing, said tubular extension along said neck region thereby being substantially reformed into said exterior surface of said parison, wherein a first outer width across said tubular extension between said longitudinal cavity and said exterior surface of said parison is less than a second outer width across said tubular extension across said longitudinal cavity, said first outer width isolating said tubular extension during said heating and pressurizing to minimize reshaping of said tubular extension during said heating and pressurizing, and said dilation element comprising a round cross-section.

13. The method according to claim 1, wherein said stretching to shrink said tubular extension against said dilation element comprises heating a middle portion of said parison.

14. The method according to claim 1, wherein said stretching to shrink said tubular extension against said dilation element comprises heating an end of said parison.

15. The method according to claim 1, further comprising initially stretching said parison before said stretching while an end of said parison is heated without heating a middle portion of said parison after said dilation element is disposed into said tubular extension, said dilation element thereby being longitudinally positioned within said tubular extension, wherein said stretching to shrink said tubular extension against said dilation element comprises heating said middle portion.

16. The method according to claim 1, wherein said mold comprises a clearance cavity receiving said tubular extension along a working diameter portion, and a first outer width across said tubular extension between said longitudinal cavity and said exterior surface of said parison is less than a second outer width across said tubular extension across said longitudinal cavity, said first outer width isolating said tubular extension during said heating and pressurizing to minimize reshaping of said tubular extension during said heating and pressurizing.

17. The method according to claim 16, wherein said mold comprises a clearance cavity at least partially receiving said tubular extension along a neck region, said clearance cavity in said neck region thereby indexing said parison to said clearance cavity along said working diameter portion, and said dilation element is entirely sealed within said tubular extension, said tubular extension being characterized by not comprising any lateral openings through said wall of said tubular extension.

18. The method according to claim 17, further comprising disposing heat shrink tubing over said tubular extension along said neck region after said heating and pressurizing, said tubular extension along said neck region thereby being substantially reformed into said exterior surface of said parison, and wherein said dilation element comprises a round cross-section.

19. The method according to claim 18, wherein said mold does not comprise any clearance cavities receiving said tubular extension along a tapered region extending to a neck region, said tubular extension thereby being compressed against said mold and substantially closing said longitudinal cavity along said tapered region, and said stretching to shrink said tubular extension against said dilation element comprises heating a middle portion of said parison.

20. The method according to claim 19, further comprising initially stretching said parison before said stretching while an end of said parison is heated without heating said middle portion of said parison after said dilation element is disposed into said tubular extension, said dilation element thereby being longitudinally positioned within said tubular extension.

* * * * *